(12) United States Patent
Wennberg et al.

(10) Patent No.: US 11,547,994 B2
(45) Date of Patent: Jan. 10, 2023

(54) SELF-CALIBRATING BILIRUBIN TEST CARD SYSTEM AND METHOD

(71) Applicant: Bilimetrix-USA LLC, Bothell, WA (US)

(72) Inventors: Richard P. Wennberg, Bothell, WA (US); Michael Koenig, Bellevue, WA (US); Fang Yuan, Mississauga (CA)

(73) Assignee: BILIMETRIX-USA LLC, Bothell, WA (US)

( * ) Notice: Subject to any disclaimer, the term of this patent is extended or adjusted under 35 U.S.C. 154(b) by 162 days.

(21) Appl. No.: 17/162,680

(22) Filed: Jan. 29, 2021

(65) Prior Publication Data

US 2021/0237053 A1 Aug. 5, 2021

Related U.S. Application Data

(60) Provisional application No. 63/094,151, filed on Oct. 20, 2020, provisional application No. 62/968,692, filed on Jan. 31, 2020.

(51) Int. Cl.
| | |
|---|---|
| *B01L 3/00* | (2006.01) |
| *G01N 33/49* | (2006.01) |
| *G06T 7/80* | (2017.01) |
| *G06T 7/13* | (2017.01) |
| *G06T 7/90* | (2017.01) |
| *G06T 7/00* | (2017.01) |

(52) U.S. Cl.
CPC .......... *B01L 3/5023* (2013.01); *G01N 33/491* (2013.01); *G06T 7/0014* (2013.01); *G06T 7/13* (2017.01); *G06T 7/80* (2017.01); *G06T 7/90* (2017.01); *B01L 2300/02* (2013.01); *B01L 2300/0681* (2013.01); *B01L 2300/0816* (2013.01); *B01L 2300/0825* (2013.01); *G06T 2207/10024* (2013.01); *G06T 2207/20132* (2013.01); *G06T 2207/30024* (2013.01)

(58) Field of Classification Search
CPC .............. B01L 3/5023; B01L 2300/02; B01L 2300/0681; B01L 2300/0816; B01L 2300/0825; G01N 33/491; G06T 7/0014; G06T 7/13; G06T 7/80; G06T 7/90; G06T 2207/10024; G06T 2207/20132; G06T 2207/30024
See application file for complete search history.

(56) References Cited

U.S. PATENT DOCUMENTS

2014/0295415 A1* 10/2014 Rolland ................... C12Q 1/68
435/6.1

* cited by examiner

*Primary Examiner* — Jennifer Wecker
*Assistant Examiner* — Alea N. Martin
(74) *Attorney, Agent, or Firm* — Womble Bond Dickinson (US) LLP

(57) ABSTRACT

A sample of blood is placed on a bilirubin test strip and plasma separated from the red blood cells. The bilirubin test strip is located on a test card along with a set of calibration images, the colors of the calibration images being associated with known plasma bilirubin levels. A photograph is taken of the test card. The bilirubin level of the blood sample is determined by, within the photograph, interpolating the color of the plasma and the colors of the closest colored calibration images.

20 Claims, 9 Drawing Sheets

SELF-CALIBRATING BILIRUBIN TEST CARD SYSTEM AND METHOD

CROSS-REFERENCE TO RELATED APPLICATIONS

This application is related to and claims priority to both U.S. Provisional Application No. 62/968,692, filed Jan. 31, 2020, entitled "Mobile Device-Based Bilirubin Calculation and Management," and U.S. Provisional Application No. 63/094,151, filed Oct. 20, 2020, entitled "Self-Calibrating Bilirubin Test Card System and Method." These applications are hereby incorporated herein by reference in their entireties and for all purposes.

BACKGROUND

Kernicterus (brain damage from severe newborn jaundice—hyperbilirubinemia) can cause cerebral palsy and neonatal death. Tragically, newborn jaundice can be easily treated upon detection. However, remote and impoverished areas of the world often do not have access to effective and affordable diagnostics. A need exists for a point-of-care self-calibrating bilirubin test card system that can be easily deployed and cost-effective.

BRIEF DESCRIPTION OF THE DRAWINGS

Various techniques will be described with reference to the drawings, in which.

DETAILED DESCRIPTION

Figure 1:
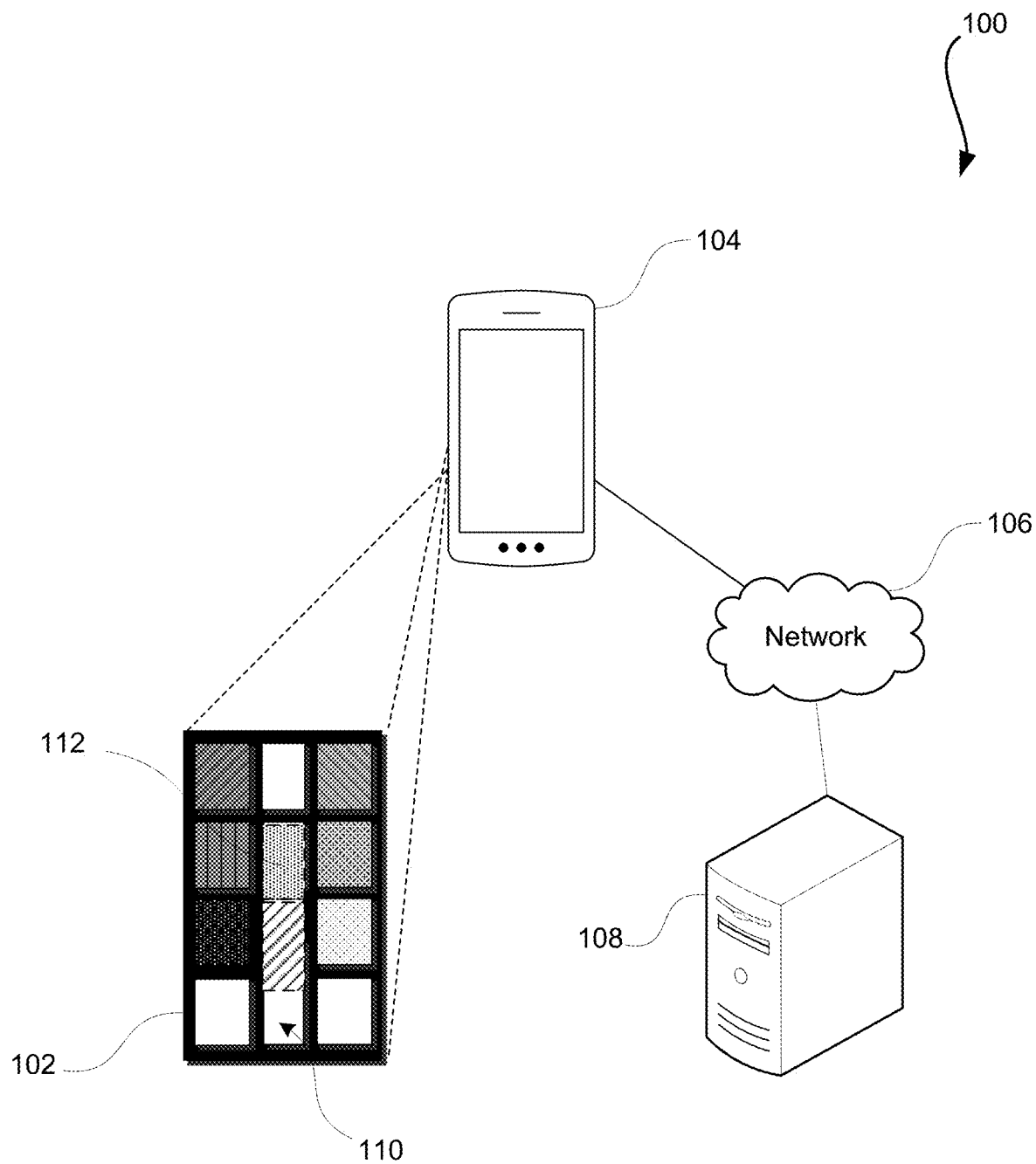
FIG. 1 shows an illustrative example of a system in which various embodiments can be implemented.

Kernicterus (brain damage from severe newborn jaundice—hyperbilirubinemia) is a common cause of cerebral palsy and neonatal death in many low-middle income countries and can be a major cause of early newborn mortality and cerebral palsy in Sub-Sahara Africa. Most babies with bilirubin induced brain injury are affected before arriving at a care facility. Thus, early detection and evaluation can be critical. Kernicterus can easily be prevented by timely treatment with phototherapy (exposure to bright lights).

Bilirubin, an orange-yellow pigment, is a waste product produced by the breakdown of heme. Heme is a component of hemoglobin, which is found in red blood cells. Bilirubin is ultimately processed by the liver so that it can be removed from the body.

During the first week of life, a higher bilirubin level can produce jaundice due to a low activity of liver enzymes required for excretion. Normal indirect bilirubin is below 5 mg/dL during the first 24 hours of birth. However, newborns with increased red cell breakdown may develop severe jaundice and dangerous bilirubin levels. It is important to identify newborns with dangerous levels of bilirubin and quickly treat them to prevent irreversible brain damage (kernicterus). The consequences of this damage include mental retardation, learning and developmental disabilities, hearing loss, eye movement problems, and death. The risk for developing kernicterus and need for treatment can be determined using a rapid point of care plasma bilirubin assay requiring a single drop of blood collected by a heel prick applied to a test strip.

Major barriers to care that may lead to kernicterus include (1) parents' failure to recognize jaundice and seek care, and (2) the inability, especially in rural clinics, to evaluate the severity of jaundice. Several established and developing companies have addressed the problem of jaundice assessment, but most effective instruments can be prohibitively expensive in rural areas where they are most needed. In addition to providing immediate bilirubin assessments, some embodiments may include the reporting of bilirubin diagnoses via telemetry to a central "Stop Kernicterus" website. In various embodiments, a website may have a hierarchy of secured accessibility ranging from public access to information about jaundice, provider access to coordinate care and a patient referral network, manager access to monitor instrument use, and program director access to gather population data and facilitate research.

A system incorporating a self-calibrating bilirubin test card that allows for the simultaneous capture of both an image of a test strip as well as images of calibration samples needed to determine the bilirubin level may provide recommendations to a technician for next steps based on artificial intelligence (AI) and machine learning (ML) algorithms.

A self-calibrating bilirubin test card may comprise, consist, or consist essentially of a bilirubin test strip attached to a bilirubin test card containing reference color samples previously calibrated with known concentrations of bilirubin. A bilirubin test strip may comprise, consist, or consist essentially of a cell/plasma separator attached in tandem with a lateral flow membrane. In an embodiment, the separator may be comprised of cellulose (including nitrocellulose), glass fiber, or synthetic materials. In an embodiment, after placing a sample of blood on a test strip, a blood/plasma separator, retaining red blood cells, may remain red while the adjacent lateral flow membrane (containing plasma) turns yellow. In an embodiment, the amount of yellow captured in a photographic image of the bilirubin test strip may represent the plasma concentration of bilirubin. The color of the sample on the test strip can be compared to a set of color samples on a test card. Such a test card can, in an embodiment, contain a collection of colored images, similar to a paint color chart, in which the colors of the images correspond to particular bilirubin levels. When evaluating the intensity of yellow to determine the bilirubin level, the photograph may need to be calibrated to accommodate optical characteristics of a particular mobile phone cameras, different lighting and shade conditions present when a photograph is taken, and concentration-dependent color properties of plasma bilirubin.

In an embodiment, an image of the test strip may be obtained and evaluated against the reference color samples on a bilirubin test card. In an embodiment, such an image may be obtained by a camera. In an embodiment, the camera may be part of a user device. When evaluating the color of the test sample to determine the bilirubin level, the picture may need to be standardized and calibrated due to the different optical characteristics of a particular mobile phone—different lighting and shade characteristics can occur with each photograph—and the overall lighting conditions. In various embodiments, standard calibration methods of first taking a photograph of a calibration card and then taking a separate photograph of the blood sample may not work because of the variances that may occur across photographs within the camera on the user device. Color values for the test sample and reference color shapes across photographs can vary with light, shadows, and the optical characteristics of the camera. Accordingly, in an embodiment, simultaneously capturing the images of the bilirubin test strip and bilirubin test card, within a single photograph, may be necessary.

In an embodiment, a self-calibrating bilirubin test card system can use a self-calibrating bilirubin test card that, within a single image, can capture the color values of the reference color shapes and simultaneously captures the color values of the bilirubin test strip containing the blood sample for analysis. In an embodiment, this may be done by placing a bilirubin test strip on the bilirubin test card and surrounding it with images having known values of color. Within the image, each of the reference color shapes may be identified and a color value assessed. The bilirubin test strip may then be located and the location of the bilirubin sample determined by mapping the shape and outline of the blood sample. The color of multiple areas of the bilirubin portion of the sample may then be calculated from the blood sample. The color of these areas of the sample may then be compared with the reference color shapes to determine the reference color shapes that are closest to the color value of the bilirubin sample. Based on the differences between the known values of the reference color shapes and the bilirubin sample, reference color shapes that bracket the bilirubin sample may be determined. The bilirubin concentration can then be interpolated from the known bilirubin concentrations associated with the bracketing reference color shapes.

In the preceding and following description, various techniques are described. For purposes of explanation, specific configurations and details are set forth in order to provide a thorough understanding of possible ways of implementing the techniques. However, it will also be apparent that the techniques described below may be practiced in different configurations without the specific details. Furthermore, well-known features may be omitted or simplified to avoid obscuring the techniques being described.

As one skilled in the art will appreciate in light of this disclosure, certain embodiments may be capable of achieving certain advantages, including some or all of the following: (1), avoiding an "impedance mismatch" between a photographic image of a bilirubin test strip and a bilirubin test card; (2) performing color comparisons between a bilirubin test strip and reference color shapes based upon the color value of the test strip and the efficacy of the comparison method; and (3) obviating the optical differences between a variety of user devices used to perform a bilirubin test.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques described and suggested include methods and systems for performing a neonatal bilirubin assessment using a mobile device, a self-calibrating bilirubin test card, and cloud services. Although the examples and illustrations used throughout this specification describe a self-calibrating bilirubin comprising a user device and a self-calibrating bilirubin test card, these examples are not intended to be limiting. Other variations are within the spirit of this disclosure. Throughout this specification, the terms "blood sample", "bilirubin sample", and "defined bilirubin area" shall be used interchangeably.

Furthermore, while the present disclosure addresses testing for yellow as a representation of bilirubin concentration, other test cards and test strips may involve other colors and other substance levels. For example, a test card system for glucose-6-phosphate dehydrogenase (G6PD) may involve a test strip oriented towards various shades of another color.

FIG. 1 shows an illustrative example of a system 100 in which various embodiments can be implemented. The system 100 comprises a user device 104 and a server 108, which can be operably connected via a network 106.

The user device 104 can include various suitable devices such as a mobile device, smartphone, laptop computer, digital camera, tablet computer, desktop computer, or the like. In an embodiment, a user device can include a camera and a touchscreen. Furthermore, a user device can include any appropriate device operable to send and/or receive requests, messages, or information over an appropriate network 106 and, in some embodiments, convey information back to a user of the user device. Examples of user devices can also include personal computers, handheld messaging devices, laptop computers, tablet computers, set-top boxes, personal data assistants, embedded computer systems, electronic book readers, and the like.

A server 108 can be a cloud-based or physical server running software that can respond to client requests on the World Wide Web. A server 108 can include web servers, database servers, content servers, collaboration servers, ftp servers, list servers, mail servers, and the like. A server 108 may process incoming network requests over HTTP and other related protocols. A primary function of a server 108 can be to store, process and deliver pages to clients. The communication between client and server may take place using the Hypertext Transfer Protocol (HTTP). Pages delivered can be most frequently HTML documents, which may include images, style sheets and scripts in addition to the text content. Multiple servers may be used for a high traffic website.

A user agent, commonly a browser or other application, can initiate communication by making a request for a specific resource using HTTP and the server 108 responds with the content of that resource or an error message if unable to do so. The user agent can reside on a user device 104. While a major function can be to serve content, a full implementation of HTTP can also include ways of receiving content from clients. This feature can be used for submitting web forms and uploading files.

In various embodiments, utilizing a server 108, the server 108 can run any of a variety of server or mid-tier applications, including Hypertext Transfer Protocol ("HTTP") servers, FTP servers, Common Gateway Interface ("CGI") servers, data servers, Java servers, Apache servers, and business application servers. The server(s) also may be capable of executing programs or scripts in response to requests from user devices, such as by executing one or more applications that may be implemented as one or more scripts or programs written in any programming language, such as Java©, C, C# or C++, or any scripting language, such as Ruby, PUP, Perl, Python or TCL, as well as combinations thereof.

The network 106 can include any appropriate network, including an intranet, the Internet, a cellular network, a local area network, a satellite network, or any other network and/or combination thereof. Components used for such a system can depend at least in part upon the type of network and/or environment selected. Many protocols and components for communicating via such a network are well known and will not be discussed in detail. Communication over the network 106 can be enabled by wired or wireless connections and combinations thereof. In this example, the network 106 can include the Internet and/or other publicly-addressable communications network, as the environment can include a server 108 for receiving requests and serving content in response thereto, although for other networks an alternative device serving a similar purpose could be used as would be apparent to one of ordinary skill in the art.

The system can further include a bilirubin test card 102 and a bilirubin test strip 110, which will be described in detail below.

In various embodiments of the system 100, a user device 104 captures an image of a self-calibrating bilirubin test card 102 containing a bilirubin test strip 110 on which a blood sample 112 has been deposited.

In an embodiment, a bilirubin test card 102 may contain a grid of reference color shapes surrounding a bilirubin test strip 110. The bilirubin test strip 110 can be a cell plasma separator that performs lateral flow plasma detection. Each color may be a shade of yellow. The grid of colors may provide a baseline for determining a percentage of bilirubin present in an infant. The bilirubin test card may possess a grid outline of rows and columns.

The user device 104 may contain a camera. In an embodiment, a user may use the user device 104 to take a photograph of the bilirubin test card 102, containing a test strip 110, upon which a blood sample 112 has been deposited. The sample can include a plasma saturated portion of the test strip 110. In an embodiment, a user may be constrained to capture the entire bilirubin test card 102 within a photographic image.

A companion website and series of cloud services can support various embodiments. In an embodiment, information from the user device 104 may be communicated across a network 106 to a server 108. Aggregating information on the server 108 can enable management of the embodiments across different clinics of an organization such as a health ministry or research university, supporting a repository of results to be used by organizations and researchers studying kernicterus. Access to a network 106 also can allow updates to be made to the user device 104. Additionally, attributes of the user device 104 may be stored on or updated from the server 108.

The RGB color model is an additive color model in which red, green, and blue light can be added together in various ways to reproduce a broad array of colors. The name of the model comes from the initials of the three additive primary colors: red, green, and blue. A purpose of the RGB color model can be the sensing, representation, and display of images in electronic systems, such as televisions and computers, though it can also be used in conventional photography. To form a color with RGB, three light beams (one red, one green, and one blue) may be superimposed (for example by emission from a black screen or by reflection from a white screen). Each of the three beams may be termed a component of that color, and each beam can have an arbitrary intensity, from fully off to fully on, in the mixture.

The RGB color model is additive in the sense that the three light beams can be added together, and their light spectra combined, wavelength for wavelength, to make the final color's spectrum. This is essentially opposite to the subtractive color model, particularly the CMY (or CMYK) color model, which applies to paints, inks, dyes, and other substances whose color depends on reflecting the light under which we see them. CMYK refers to the four ink plates used in some color printing: cyan, magenta, yellow, and key (black). Because of properties, combination of the three light beams creates white. This can be in stark contrast to physical colors, such as dyes, that create black when mixed.

Zero intensity for each component gives the darkest color (no light, considered the black), and full intensity of each gives a white; the quality of this white depends on the nature of the primary light sources, but if they are properly balanced, the result can be a neutral white matching the system's white point. A white point (often referred to as reference white or target white in technical documents) can be a set of tristimulus values or chromaticity coordinates that serve to define the color "white" in image capture, encoding, or reproduction. Depending on the application, different definitions of white are needed to give acceptable results. For example, photographs taken indoors may be lit by incandescent lights, which are relatively orange compared to daylight. Defining "white" as daylight can give unacceptable results when attempting to color-correct a photograph taken with incandescent lighting. When the intensities for all the components are the same, the result can be a shade of gray, darker or lighter depending on the intensity. When the intensities are different, the result can be a colorized hue, more or less saturated depending on the difference of the strongest and weakest of the intensities of the primary colors employed. Each color component value can be written as a percentage, from 0% to 100%. For example, pure yellow can have an RGB value of (255, 255, 0). Under the RGB model, yellow can have red and green component values of 255 and a blue component value that varies from 0 to 255.

The HSV color model (hue, saturation, value), also referred to as HSL (hue, saturation, lightness), is an alternative representation of the RGB color model, designed in the 1970s by computer graphics researchers to more closely align with the way human vision perceives color-making attributes. In these models, colors of each hue can be arranged in a radial slice, around a central axis of neutral colors which ranges from black at the bottom to white at the top. The HSV representation models the way paints of different colors mix together, with the saturation dimension resembling various tints of brightly colored paint, and the value dimension resembling the mixture of those paints with varying amounts of black or white paint.

An increasing yellow color can manifest itself as a decrease in the blue component of RGB and an increase in the saturation component of HSV. Bilirubin can be predominantly yellow, and at high levels, saturation may become 100% under certain light conditions or quality of camera. Under such circumstances, discriminating between two samples of color using HSV can be difficult in some examples and the use of RGB analysis can provide superior results in various embodiments.

Figure 2:
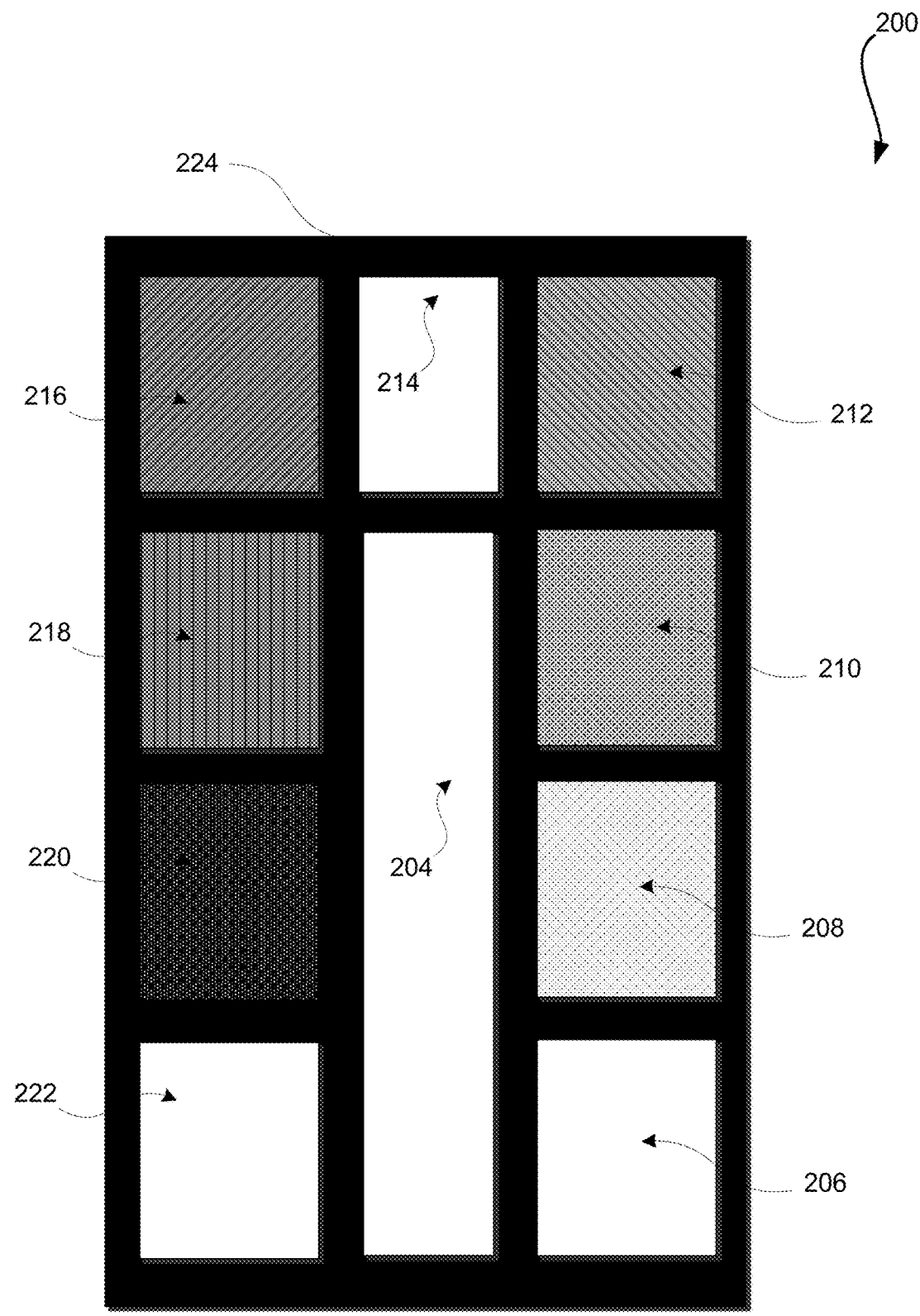
FIG. 2 is an exemplary diagram illustrating an embodiment of a self-calibrating bilirubin test card.

FIG. 2 shows an illustrative example of a bilirubin self-calibrating bilirubin test card 200. In an embodiment, the bilirubin test card 200 can include a bilirubin test strip 204 surrounded by a set of reference color shapes 206-222. Each of the reference color shapes 206-212 and 216-222 may correspond to an experimentally assigned plasma bilirubin concentration values. In an embodiment, the subset of reference color shapes 208, 210, 212, 216, 218, and 220 may correspond to increasing levels of bilirubin. As an example, in an embodiment, reference color shape 208 may have an HSV value of (60, 20, 100), an RGB value of (255, 255, 204), and correspond to a bilirubin level of 0.2 mg/dL. Also, in the embodiment, reference color shapes 210, 221, 216, 218, and 220 may have HSV values of (60, 51, 100), (61, 62, 97), (60, 100, 93), (47, 64, 98), and (48, 90, 97), and RGB values of (255, 255, 125), (245, 247, 94), (237, 237, 0), (250, 215, 90), and (247, 203, 25), respectively. Furthermore, in the embodiment, reference color shapes 210, 221, 216, 218, and 220 may correspond to bilirubin values of 5.4, 10.0, 15.4, 21.5, 26.0, and 29.8 mg/dL, respectively.

In an embodiment, the reference color shapes 206-212 and 216-222 can have increasing values of yellow, with reference color shape 208 being the lightest and reference color shape 220 being the darkest. In an embodiment, the yellowness can increase from reference color shapes 208 to 212 and 216 to 220 in a counter-clockwise direction beginning with reference color shape 208 and ending with reference color shape 220. Alternatively, in an embodiment, the yellowness and saturation can increase from reference color shapes 220 to 216 and 212 to 208 in a clockwise direction beginning with reference color shape 220 and ending with reference color shape 208. The reference color shapes 206-222 may also be referenced as calibration images. In an embodiment, some of the reference color shapes 206, 214, 222 may be white, and have an HSV value of (0-255, 0-255, 255) and an RGB value of (255, 255, 255). Interspersing white calibration images 206, 214, and 222 among the yellow calibration images 206-212 and 216-222, in an embodiment, can provide additional contrast with yellow calibration images 206-212 and 216-222, resulting in better accuracy of the comparison of the bilirubin sample with the reference color shapes. White calibration images can also be used, in an embodiment, for color balancing under some light conditions. Other reference color shapes 208, 210, 212, 216, 218, 220 may have different color values. In an embodiment, the test strip 204 and the reference color shapes 206-222 may be set in a grid 224, the grid possessing a color of such contrast with the test strip 204 and the reference color shapes 206-222 that the boundaries of the test strip 204 and the reference color shapes 206-222 can be clearly delineated. The grid 224 may be black and possess an HSV value of (0-255, 0-255, 0) and an RGB value of (0, 0, 0). In an embodiment, the reference color shapes may be adjusted to represent closer bilirubin concentration levels as the amount of bilirubin in the test strip increases. In an embodiment, this can acknowledge that with higher levels of bilirubin, corresponding changes in RGB and HSV may be smaller.

In another embodiment, the reference bilirubin test card may not contain a grid. In an embodiment, the user device can locate and identify the reference color shapes and the test strip by having the X/Y coordinates and dimensions of the reference color shapes and the test strip communicated to the user device. Different configurations and orientations of bilirubin test cards can be employed for different user devices having different camera capabilities.

In an embodiment, a self-calibrating bilirubin test card 200 may contain a grid of reference color shapes 206-222 surrounding a bilirubin test strip 204. Each color may be a shade of yellow. The grid of colors may provide a baseline for determining a percentage of bilirubin present in an infant. The grid outline may be structured as rows and columns. The saturation component of the HSV values of the reference color shapes may increase with adjacent reference color shapes 208, 210, 212, 216, 218, and 220. The red and green elements of the RGB value of the reference color shapes may increase with adjacent reference color shapes 208, 210, 212, 216, 218, 220. The blue component of the RGB value of the reference color shapes may decrease with adjacent reference color shapes 208, 210, 212, 216, 218, 220. The reference color shapes 206-222 may be at known locations on the bilirubin test card 200. The reference color shapes may be in the forms of squares, rectangles, dots, triangles, or any other shape. Furthermore, there may be any number of reference color shapes on a bilirubin test card. For example, in an embodiment, the greater the number of reference color shapes, the smaller the difference may be between the colors of the reference color shapes, and the more accurate a bilirubin level can be obtained. In an embodiment, a bilirubin test card 200 with a single reference color shape can be used. Such a bilirubin test card could provide a threshold test for bilirubin, i.e., does the bilirubin level of the blood sample exceed that of the reference color shape. In other words, is the color of the bilirubin portion of the blood sample simply "more yellow" than the reference color shape? Such a bilirubin test card could be used for a simple "Normal/Abnormal" test.

In another embodiment, the greater the number of reference color shapes on the bilirubin test card, the smaller the color difference may be between the sample and the bounding reference color shapes. Thus, in an embodiment, the range between the bilirubin levels associated with the bounding color shapes may be smaller.

In an embodiment, the bilirubin test card 200 can be made of semi-gloss paper, although a bilirubin test card can be constructed from any type of paper, plastic, metal, or other substance. In an embodiment, the bilirubin test card can be reusable, with detachable or replaceable reference color shapes. The bilirubin test card may also employ a detachable test strip, with a new test strip attached for each test. In an embodiment, a bilirubin test card may have any dimensions that allow its image to be captured by the camera of a user device. For example, a bilirubin test card may be rectangular or circular.

Figure 3:
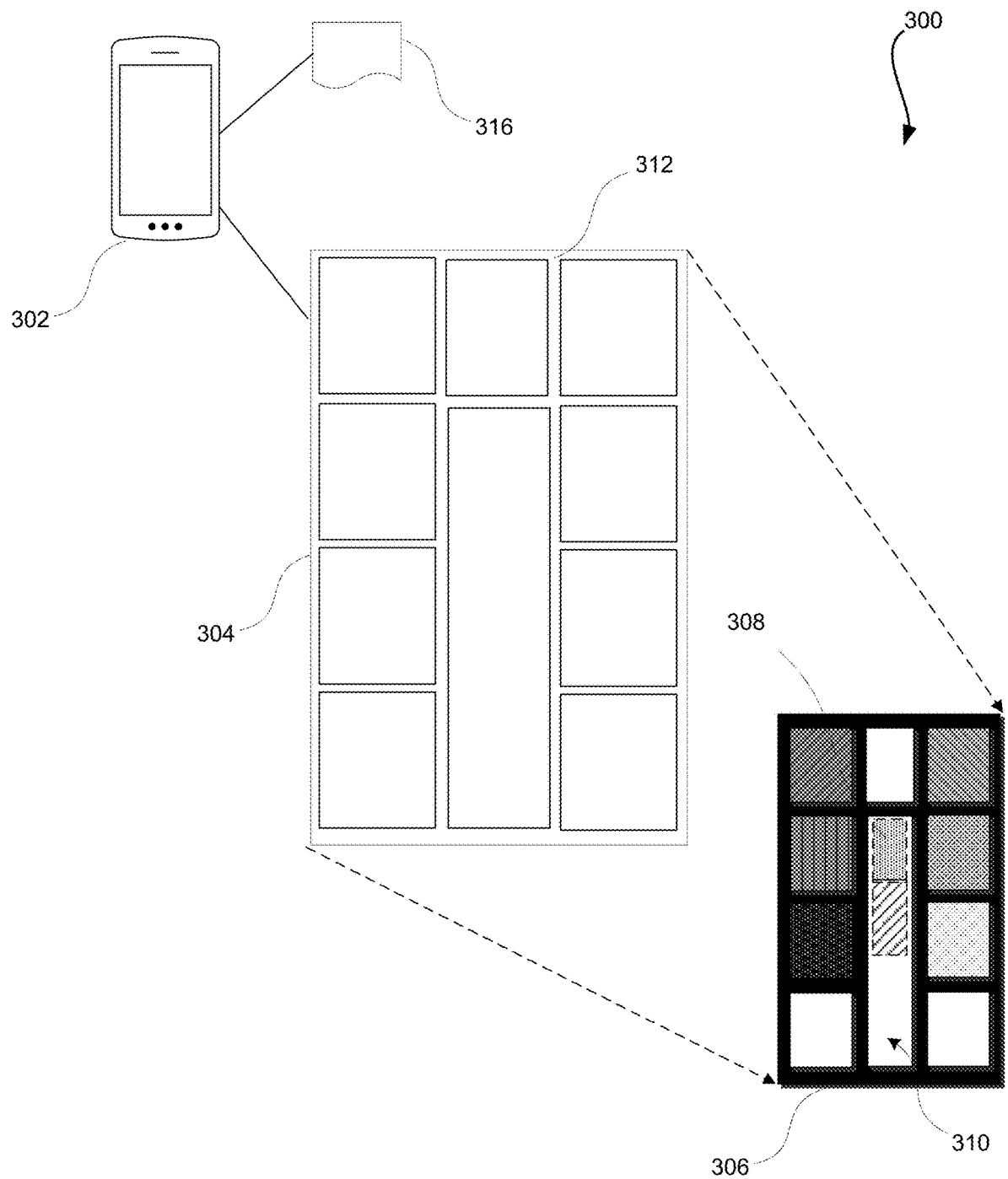
FIG. 3 is an exemplary diagram of an embodiment of a self-calibrating bilirubin test card in which a screen image of the bilirubin test card has been captured by a camera on a user device.

FIG. 3 shows an illustrative example of a system 300 in which various embodiments can be implemented. In the system 300, a user device 302 can capture an image of a self-calibrating bilirubin test card 306. Acquisition of the screen image 304 may be aided by the use of a grid 312 that can overlay the screen image 304, centering the reference color shapes 206-222 within elements of the grid 312 such that the reference color shapes can be distinguished from the grid 312.

For example, in one embodiment, the user device 302 can present on a display of the user device 302 a screen grid 312 overlaid over a real-time or captured image obtained from the camera of the user device 302 with the screen grid 302 having portions that can be transparent and/or translucent such that a real-time image or image captured by the camera of the user device 302 can be seen through, and aligned with, the grid 312. The screen grid 312 can correspond to the test card grid 224 of the bilirubin test card 200 such that a user can move the user device 302 (e.g., up, down, left, right, and rotated) such that the screen grid 312 can be aligned with and matches the size of the test card grid 224 in a real-time image of the bilirubin test card 200 presented on the display of the user device 302. This can allow a user to capture a suitable image of the bilirubin test card 200 of an appropriate size and orientation that can include the bilirubin test strip and the reference color shapes. The user device 302 may also automate the alignment of the screen grid 312 with the test card grid 224. For example, in an embodiment, if the user device is unable to align the screen grid 312 with the test card grid 224, a user of the user device may be alerted as to the error. In an embodiment, the user device can initiate a sequence of photographs until it recognizes a proper framing of the bilirubin test card 306. In an embodiment, the user device can use previously captured photographic images.

In an embodiment, the bilirubin test card 306 contains a bilirubin test strip 310. The bilirubin test strip 310 may comprise, consist, or consist essentially of a cell/plasma separation membrane attached in tandem with a lateral flow membrane 308 on which a blood sample has been deposited. In an embodiment, the lateral flow strip may be comprised of nitrocellulose. In some embodiments, after placing a sample of blood on the bilirubin test strip, the portion of the strip in front of the cell/plasma separation membrane, retaining red blood cells, can remain red while the adjacent lateral flow membrane can be saturated with plasma and turn yellow. In an embodiment, the amount of yellow captured in a photograph may represent the concentration of bilirubin on the lateral flow membrane 308. The bilirubin test card 306 can further include a set of reference color shapes 206-222. The reference color shapes 206-222 can be arranged so as to enclose the test strip 310. In an embodiment, the test strip 310 and reference color shapes 206-222 can be placed anywhere on the bilirubin test card 306 so long as their location can be communicated to the user device 302 and the known color values and associated bilirubin values of the individual reference color shapes 206-222 conveyed to the user device 302. In an embodiment, the user device locates the test strip 310 and reference color shapes 206-222 on the bilirubin test card 306, and identifies the two reference color shapes that have color values closest to that of the bilirubin area of the lateral flow membrane 308. In an embodiment, more than two reference color shapes may be used to determine the bilirubin level of the plasma portion of the lateral flow membrane 308. In various embodiments, any number of two or more reference color shapes can be used.

Upon capturing a screen image 304 that can include the bilirubin test card 306, the bilirubin test strip 310, the red blood cells and separated plasma on the lateral flow membrane 308, and the reference color shapes 206-222, each pixel of the screen image 304 may be evaluated. In some embodiments, all the pixels of the original photo may not be needed in order to calculate the bilirubin level. A user device containing a high quality camera may produce images with a high pixel density. For example, in an embodiment, the application may not need the pixel density of the original screen image and may reduce the pixel density of the screen image 304. A higher pixel density means that there can be more pixels in the same amount of physical space. Downsampling averages adjacent regions of pixels to reduce information without making it blurry, and can be typical with high-resolution images, such as those captured by an iPhone or digital camera, where a reduction of the image's size and resultant storage can be desired. With respect to the reference color shapes, only a few pixels may be required from each of the reference color shapes, as the color of their pixels should be uniform. In an embodiment, the user device 302 can automatically reduce the pixel density of the screen image 304. Alternatively, the user of the user device can manually reduce the pixel density. In another embodiment, the user of the user device can specify a target file size resulting in an associated pixel density reduction.

Furthermore, the screen image may also be cropped to eliminate extraneous portions of the of the screen image 304. In an embodiment, the screen image may be cropped to restrict the image to that of the bilirubin test card 306. The screen image 304 may be further cropped to reduce the size of the reference color shapes, as the color of their pixels should be uniform. Consequently, in an embodiment, only a small portion of the reference color shapes may be retained in the screen image 304. In an embodiment, the portion of the test strip 310 above the red blood cell/plasma separator can be cropped. In another embodiment, the screen image 304 may be cropped so as to only include a few pixels of the upper left corner of reference color shape 206, the left edges of reference color shapes 208 and 210, the lower left corner of reference color shape 212, the bottom edge of reference color shape 214, the lower right corner of reference color shape 216, the right edges of reference color shapes 218 and 220, and the upper right corner of reference color shape 222. The screen image may then be saved to an image file 316 on the user device. In an embodiment, the image file may be uploaded to a server. In an embodiment, the image file may be uploaded to a database.

In an embodiment, the image file 316 may be converted to a binary image containing only black or white pixels. In an embodiment, this can allow detection and determination of the dimensions and geometries of the grid 224 of the bilirubin test card. After creating a black and white image, the borders of the bilirubin test strip 310 may be identified. In an embodiment, by creating a binary image and establishing true black, the boundaries of the left, top, and right edges of the test strip 310 may be identified within the image file 316. In an embodiment, determination of the boundaries of the test strip 310 may be performed before writing the image file 316. In another embodiment, the image file 316 may be converted to a greyscale image. In an embodiment, exception checks may be employed to ensure the presence of a test strip, by determining whether the dimensions of the test strip 310 fall within an expected width and height range.

After the test strip has been validated and delimited within the image file 316, in an embodiment, the test strip 310 may be rescanned to determine the perimeter of the blood portion of the image and exclude it from further scanning, resulting in a defined bilirubin area in which the test strip has turned yellow. In an embodiment, in the binary version of the image file 316, the blood/plasma separator may be black. In an embodiment, the portion of the test strip 310 containing blood may be excluded from further scanning. The plasma area of the lateral flow membrane 308 may then be further scanned to identify a number of consecutive pixels for which the color has remained constant. Scanning may commence from the outer edges of the defined bilirubin region of the lateral flow membrane 308 and stop after determining that the color of a number of consecutive pixels has remained constant. In another embodiment, scanning may commence from the inner edges of the defined bilirubin region. In an embodiment, the scan may check for a particular number of consecutive pixels of consistent color.

In an embodiment, color values may be determined for different parts of the defined bilirubin area of the lateral flow membrane 308. Color values may be determined for a top section, a left or right section, or any combination of the top, left, and right sections. To calculate a value for the top section, the top section of the bilirubin test strip 310 may be bounded and the average color values of the pixels contained therein determined. To determine the areas of the top, left, and right sections, in an embodiment, a specific number of pixels from the top, and from each of the left and right edges of a section may be examined. The depth of pixels examined may differ between the top and the sides. The average color values of a section, in an embodiment, may then be determined. In an embodiment, both HSV and RGB values may be determined.

The reference color shapes 206-222, or calibration images, may be identified within the image file 316 and one or more color values determined. In an embodiment, only a subset of pixels of the reference color shapes 206-222 may be retained in the screen image 304 or the image file 316. In an embodiment, for example, 4×4 pixel color samples can be retained for each of the reference color shapes. The average color values of each sample can then be calculated. In an embodiment, because the reference color shapes 206-222 and plasma portion of the lateral flow membrane 308 have been captured in the same screen image 304, any skew of color due to shadow, reflection, ambient light, etc., can be equally applied to all of the screen image elements.

In an embodiment, within the image file 316, the color value of the blood sample may then be compared with the color values of the reference color shapes 206-222. This may be achieved by determining, for each reference color shape, the color difference between the reference color shape and the plasma portion of the lateral flow membrane 308. In an embodiment, the reference color shape 206-222 whose color is closest in value to that of the plasma area of the lateral flow membrane 308 may be used as a baseline to determine a bilirubin level of the plasma. The color difference may be expressed as either an HSV or RGB value. In an embodiment, the lightest yellow colored reference color shape may be reference color shape 208 and may be in a lower position in the rightmost column on the bilirubin test card. In an embodiment, the darkest yellow colored reference color shape may be located in a lower position on the leftmost column on the bilirubin test card. In an embodiment, the bilirubin level may be calculated by determining the color differences between the plasma portion of the lateral flow membrane 308 and the two reference color shapes whose color values are closest to that of the plasma portion of the lateral flow membrane 308, the reference color shapes each assigned bilirubin reference values. The color difference can be the difference between the HSV values or RGB values of the bilirubin area of the blood sample and those of a given reference color shape.

Figure 4:
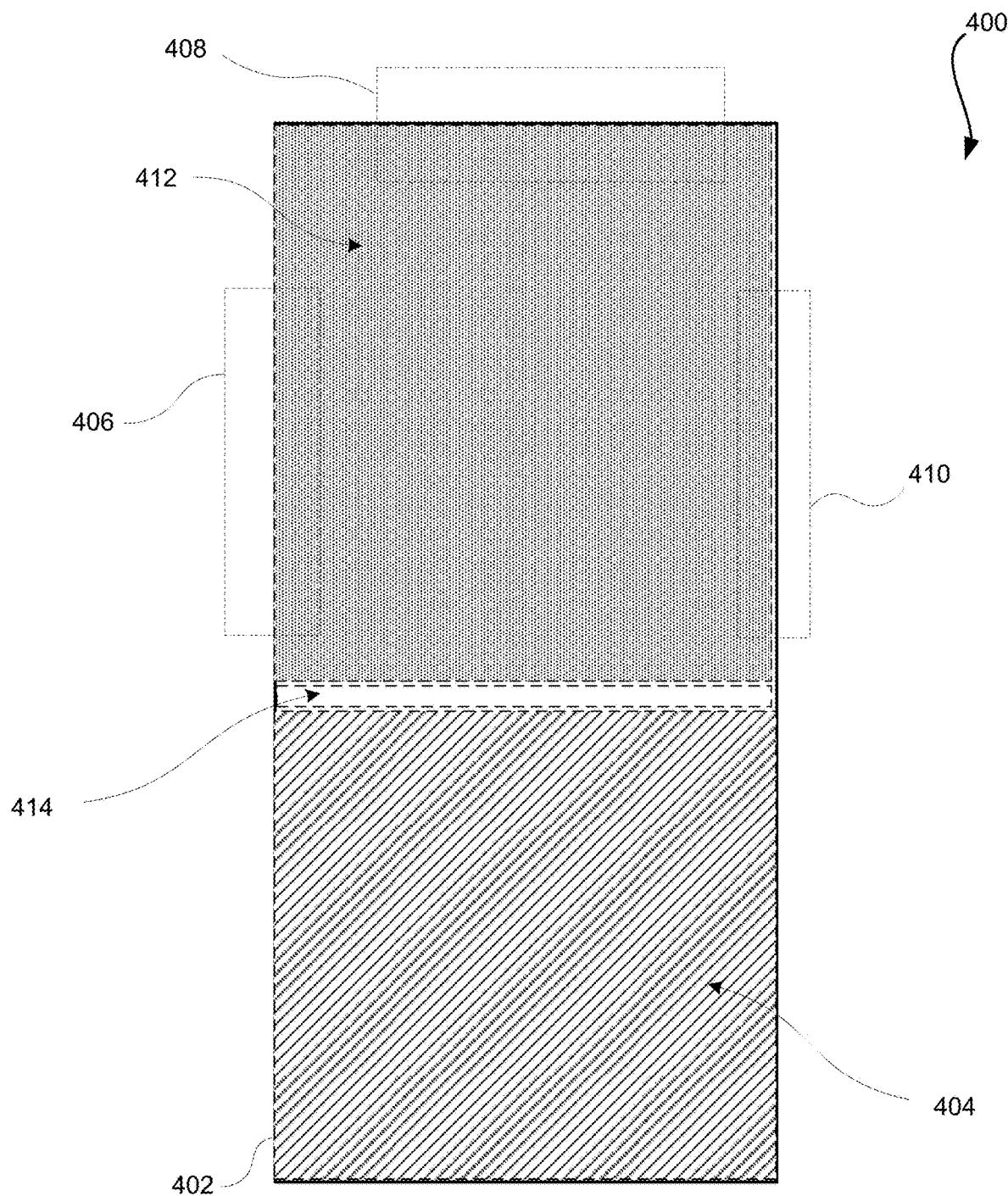
FIG. 4 is an exemplary diagram of an embodiment of a bilirubin test strip on which a blood sample has been deposited.

FIG. 4 shows an illustrative example 400 of a section of a test strip 402 upon which a blood sample 404 containing red blood cells has been deposited. In an embodiment, the test strip can include a blood/plasma separator. In an embodiment, the test strip 402 can be rectangular. In other embodiments, the test strip may take other shapes, e.g., square, oval, circular. Plasma can be filtered from the blood 404 by a blood/plasma separator 414 and transferred by diffusion to an adjacent portion of the test strip 400, resulting in a plasma/bilirubin portion 412 of the test strip 400. The plasma/bilirubin portion 412 of the test strip can comprise a nitrocellulose membrane. In other embodiments, the plasma/bilirubin portion 412 of the test strip can comprise other substances capable of diffusing the plasma. The bilirubin portion 412 of the test strip can be yellow. The color values of the areas of the left edge 406, top edge 408, and right edge 410 of the bilirubin portion 412 of the test strip 400 can be determined by evaluating the pixels of the respective areas.

Bilirubin may not be consistent across the entire bilirubin portion of the test strip 412, as bilirubin migrates across the test strip over time. The sample may tend towards a curved shape rather than a solid rectangle. After the test strip 402 has been delimited, it may be scanned to detect color changes that represent the boundaries of the bilirubin portion 412 of the test strip 400. Scanning of the bilirubin portion 412 may stop after determining that the color of a number of consecutive pixels has remained constant. In an embodiment, a scan may first convert the pixels representing the aggregated areas of the bilirubin portion 412 and the blood sample 404 to black or white in order to determine the colored area. A subsequent scan may determine the actual color values of the pixels of the bilirubin portion 412 of the test strip 400.

In an embodiment, color values may be determined for different parts of the bilirubin portion 412. A color value may be determined for a top edge 408, a left edge 406, a right edge 410, or the any combination of the top edge 408, left edge 406, and right edge 410. To calculate a top edge, a top edge of the bilirubin test strip 310 may be identified and the average color values of the yellow pixels contained therein determined. In an embodiment, either HSV or RGB values may be determined. In an embodiment, both HSV and RGB values may be determined. To determine the area of the top, left, and right edges, in an embodiment, a specific number of pixels from the top, and from each of the leftmost and rightmost pixels of an edge may be examined. The depth of pixels examined may differ between the top, left, and right edges. Average color values of an edge, in an embodiment, may be determined.

Figure 5:
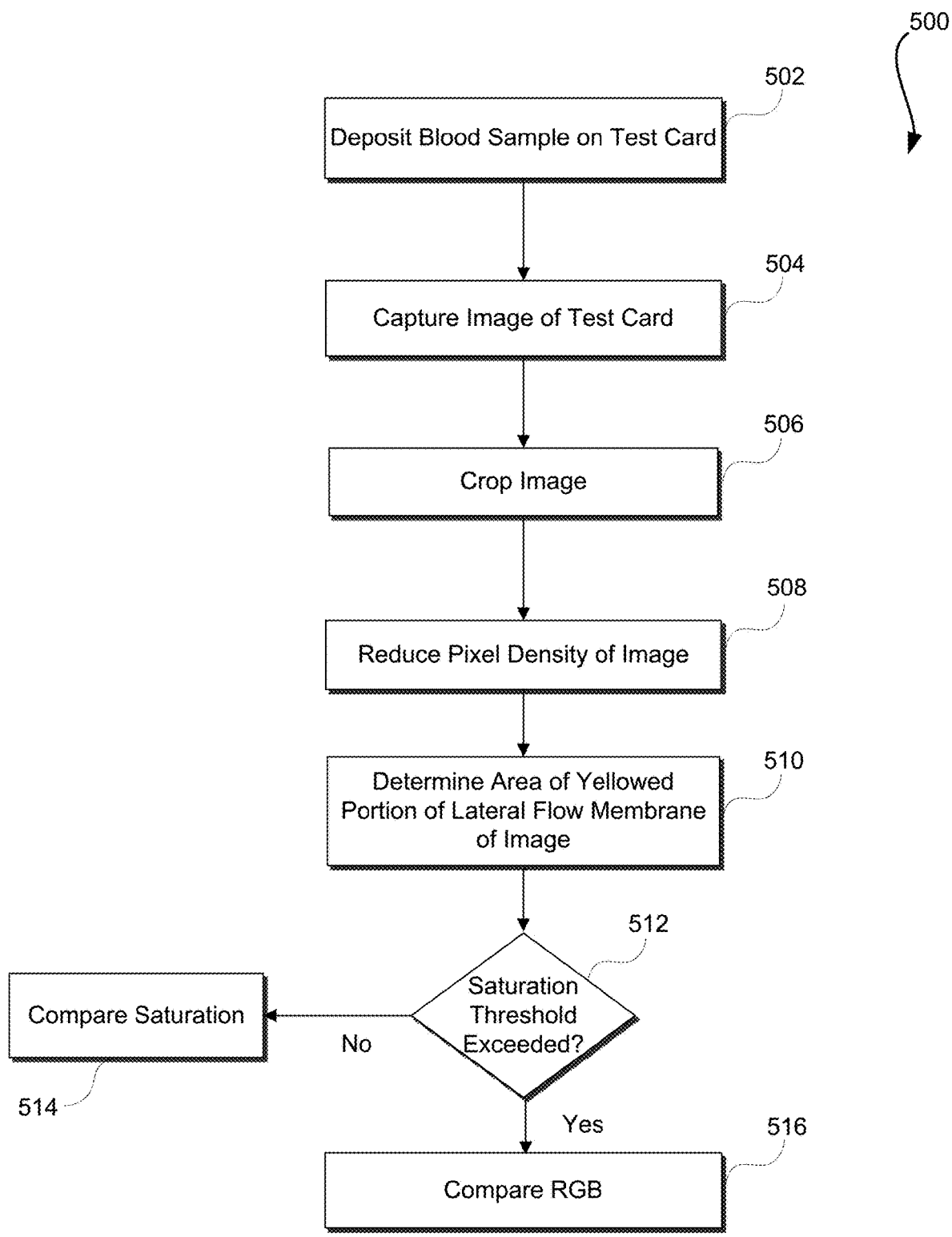
FIG. 5 shows an exemplary process for determining whether a hue/saturation/value (HSV) or red/green/blue (RGB) color model can be used to determine the bilirubin level in a blood sample in accordance with at least one embodiment.

FIG. 5 shows an illustrative example of a process 500 for determining whether an HSV or RGB color model can be used to determine the bilirubin level in a blood sample in accordance with at least one embodiment. In an embodiment, a blood sample can be deposited 502 on a bilirubin test strip on a self-calibrating bilirubin test card. The bilirubin test strip may comprise a red blood cell/plasma separator attached in tandem with a lateral flow membrane. After placing a sample of blood on a test strip, the portion of the test strip in front of the separator membrane, retaining red blood cells, can remain red while the blood plasma flows through to an adjacent lateral flow strip. In an embodiment, the plasma separator may be comprised of another material, e.g., polyvinylidene difluoride (PVDF). In another embodiment, the plasma separator may be comprised of glass fiber. The presence of bilirubin in the plasma may represent itself as a yellowish tint.

The bilirubin test card may also contain a set of colored images, similar to a paint color chart, in which the colors of the images correspond to particular bilirubin levels. In an embodiment, the colored images, or reference color shapes, may surround the bilirubin test strip. Alternatively, the reference color shapes may be arranged in any configuration, in any sequence, on the bilirubin test card. In an embodiment, the user device can identify the configuration of the bilirubin test card and the particular reference color shapes. In an embodiment, the user device can identify the bilirubin test strip. In an embodiment, a different number of white reference color shapes at the top and bottom of the bilirubin test card can indicate the proper orientation of the bilirubin test card. In an embodiment, markings on the bilirubin test card can indicate the proper orientation of the bilirubin test card. In an embodiment, the shape of the bilirubin test card can indicate the proper orientation of the bilirubin test card.

In an embodiment, the shape of the reference color shapes on the bilirubin test card can indicate the proper orientation of the bilirubin test card.

For example, in an embodiment, a bilirubin test card may be configured with a bilirubin test strip, surrounded by reference color shapes, as in FIG. 2. The reference color shapes may represent specific plasma bilirubin concentrations with color values assigned and confirmed experimentally using known bilirubin concentrations and measured under controlled lighting conditions. The colors of elements within an image may change using different light and camera conditions, but relative values change little, allowing for auto-calibration of reference color shapes and test results. In an embodiment, the user device can be informed that reference color shape 208 has an HSV value of (60, 20, 100) and an RGB value of (255, 255, 204). Similarly, in an embodiment, the user device can be informed that reference color shapes 210, 212, 216, 218, and 220 have HSV values of (60, 51, 100), (61, 62, 97), (60, 100, 93), (47, 64, 98), and (48, 90, 97), respectively. The user device can be further informed that reference color shapes 210, 212, 216, 218, and 220 have RGB values of (255, 255, 125), (245, 247, 94), (237, 237, 0), (250, 215, 90), and (247, 203, 25), respectively. Similarly, in an embodiment, the user device can be further informed that reference color shapes 206, 214, and 222 have HSV and RGB values of (0, 0, 255) and (255, 255, 255), respectively.

Figure 9:
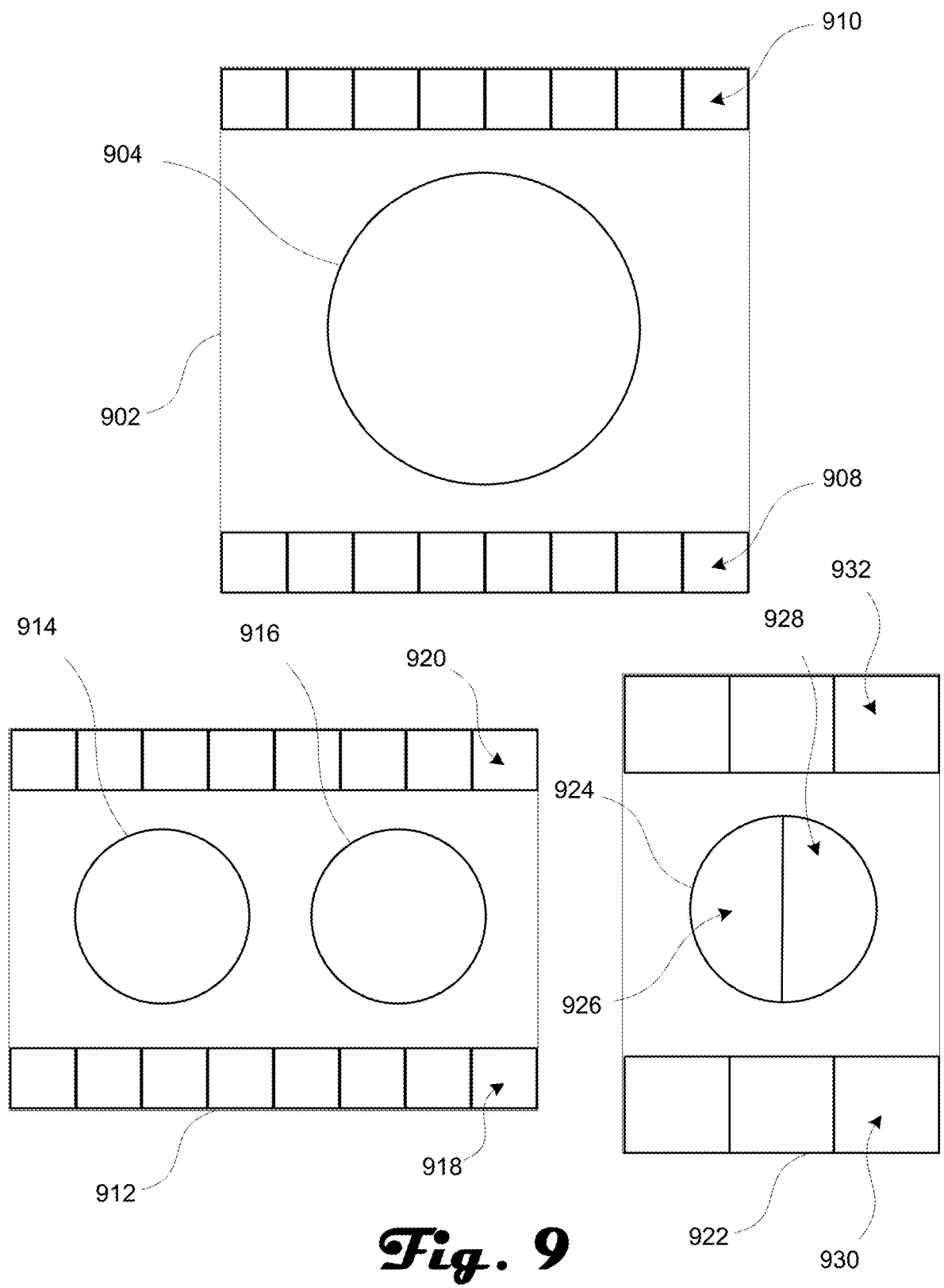
FIG. 9 is an exemplary diagram illustrating multiple embodiments of self-calibrating bilirubin test cards.

In another embodiment, similar to that of the example bilirubin test card 902 of FIG. 9, the reference color shapes may be arranged in one or more rows. As long as the location, dimensions, and HSV/RGB values of the reference color shapes can be communicated to the user device, in an embodiment, the reference color shapes may be located anywhere on the bilirubin test card. Similarly, as long as the location and dimensions of the bilirubin test strip can be communicated to the user device, the bilirubin test strip can be located anywhere on the bilirubin test card. In an embodiment, white reference color shapes having an HSV value of (0-255, 0-255, 255) or an RGB value of (255, 255, 255) may be interspersed with the other reference color shapes.

Returning to the example process 500 of FIG. 5, an image of the bilirubin test card can then be captured 504 using a camera of a user device. In an embodiment, acquisition of the image may be aided by the use of a grid on a display of the user device upon which the image can be overlaid, centering reference color shapes within elements of the grid such that the reference color shapes can be distinguished from the grid. In an embodiment, a grid on the bilirubin test card itself may be aligned with the grid on the display of the user device. In an embodiment, the image of the bilirubin test card may be validated by the user. Alternatively, the image of the bilirubin test card may be validated through the use of computer vision techniques on the user device. The bilirubin test card may contain a bilirubin test strip on which a blood sample has been deposited. As a result of red blood cells being trapped by a separation filter 414, a downstream portion 412 of the bilirubin test strip to which plasma has migrated may be a shade of yellow, an example of which can be seen in FIG. 4. The image of the bilirubin test card, in an embodiment, contains the yellow portion of the bilirubin test strip and a sufficient portion of the reference color shapes to identify them and determine their color values. In an embodiment, the image of the bilirubin test card may be stored for later analysis.

The image may be cropped 506 to eliminate extraneous portions of the image. In an embodiment, the image may be cropped to restrict the image to that of the bilirubin test card. Cropping the image may, in an embodiment, reduce the memory and storage requirements for the image.

Figure 6:
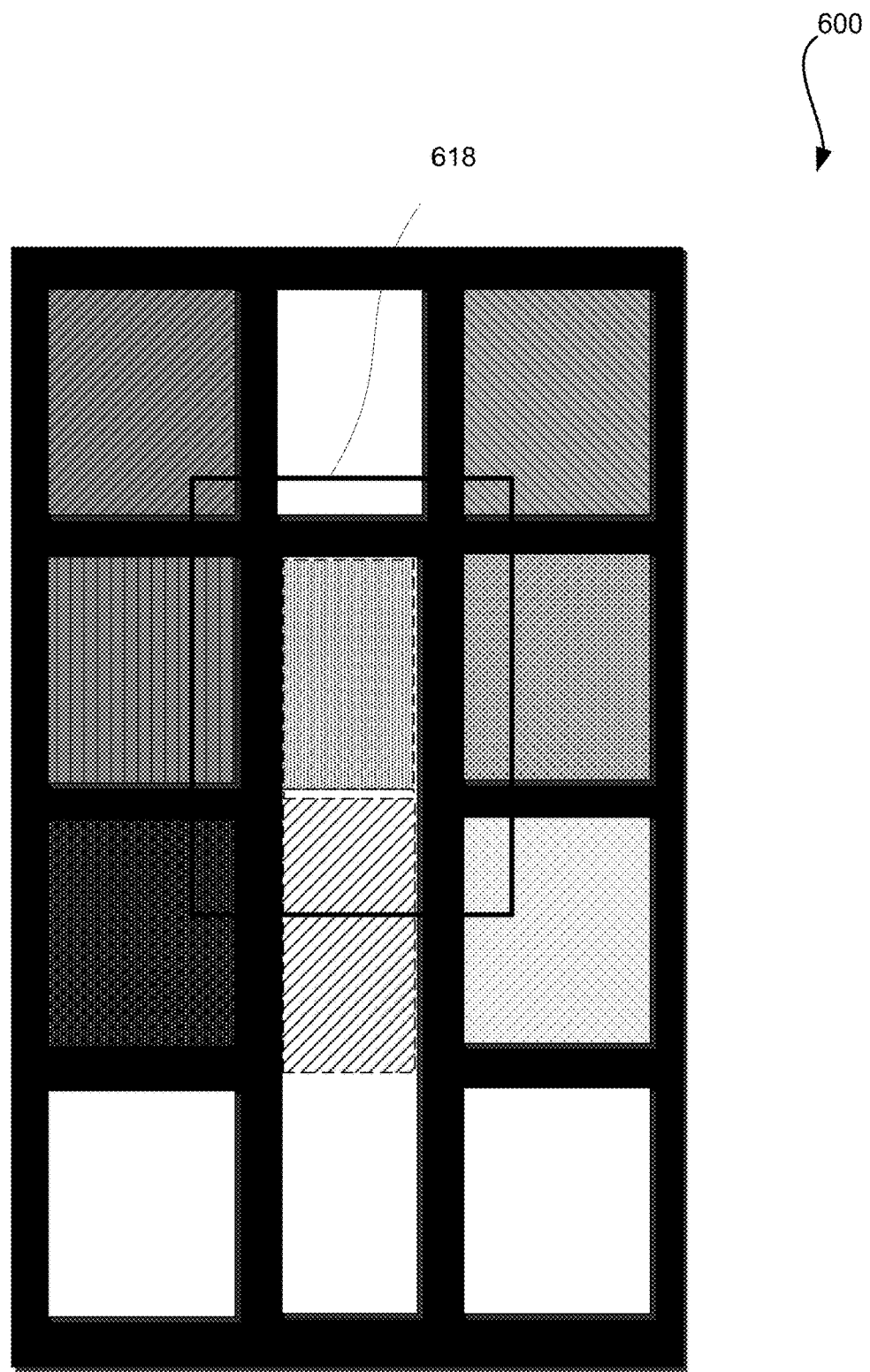
FIG. 6 is an exemplary diagram of a self-calibrating bilirubin test card that has been cropped in accordance with at least one embodiment.

In an embodiment, the image may be cropped to the outline of the bilirubin test card. In another embodiment, the image may be cropped to a minimum size that retains the yellow portion of the bilirubin test strip containing plasma and portions of the reference color shapes sufficient to identify the reference color shapes and determine their color values in the image. In an embodiment, cropping the image can reduce the resultant size of the image for storage. In an embodiment, any type of cropping can be performed that retains the yellow portion of the bilirubin test strip and representative portions of the reference color shapes. In an embodiment, cropping may be performed by the user. Alternatively, cropping the bilirubin test card may be performed through the use of computer vision techniques on the user device. FIG. 6 illustrates an example, in an embodiment, of cropping the bilirubin test card embodiment of FIG. 2. In the example, a bilirubin test card 600 has been cropped to a cropped image area 618 that can include the defined bilirubin area, the blood sample, and reference color shapes 208-220. In an embodiment, some reference color shapes can be omitted from the cropped image 618. In another embodiment, a subset of pixels from the center of the reference color shapes may be used.

The pixel density of the cropped image may be reduced 508. Analysis of the bilirubin test card may not require all of the pixels of the cropped image. Consequently, a subset of the total pixels of the blood sample on the test strip and those on the reference color shapes may be retained for subsequent comparison. For example, in an embodiment, only 25% of the pixels of the cropped image may be needed. In an embodiment, techniques such as bilinear interpolation, bicubic interpolation, box sampling, mipmaps, Fourier transforms, hqx and other pixel-art scaling algorithms may be employed. In an embodiment, the pixel density reduction further reduces the size of the image in memory and for subsequent storage. In another embodiment, pixel density can be reduced to a common density for more consistent comparison with other images. In yet another embodiment, reduction to a common pixel density facilitates the use of machine learning to improve the ability of the system to assign a value to the color of the defined bilirubin area of the bilirubin test strip and to compare it to the reference color shapes.

The area of the defined bilirubin area on the bilirubin strip can be determined 510. By applying a binary function model, the edges of the bilirubin test strip may be determined. In an embodiment, by using the grid of the bilirubin test card, the binary function model can establish the left, right, and top edges of the bilirubin test strip. Alternatively, in another embodiment, the bilirubin test card communicates the coordinates of the test strip to the user device. In an embodiment, a subsequent application of a binary function model can then establish, within the bilirubin test strip, the boundaries of the defined bilirubin area. After determining the boundaries of the blood sample, color values, both HSV and RGB, for the defined bilirubin area may be obtained.

In an embodiment, the user device can begin scanning from the outer edges of the defined bilirubin area inward. In another embodiment, the user device can begin scanning from the inner edges of the defined bilirubin area outward. The scan can continue until a particular number of pixels report a consistent color value. For example, in an embodiment, the results of a scan may indicate that ten consecutive pixels, in either a horizontal or vertical direction, can be determined to have a constant RGB value of (255, 255, 200).

In another embodiment, the results of a scan may indicate that ten consecutive pixels, in either a horizontal or vertical direction, can be determined to have a constant HSV value of (60, 51, 100). Alternatively a scan may determine that the blue component of the RGB values remains within a range across a consecutive number of examined pixels. In an embodiment, a valid range of pixel values may be five. Other valid ranges of consecutive pixel color values may establish a color value.

As another example, the results of a scan may indicate that five consecutive pixels with identical $RGB_{red}$ and $RGB_{green}$ components have $RGB_{blue}$ component values of 200, 201, 205, 199, and 198. If, in an embodiment, five consecutive pixel values within a range of five constitutes a successful scan, an average pixel RGB value may be calculated. In another embodiment, a deviation from the average blue component value may be used as a threshold to determine blue component value stability. For example, if the blue component value of the color of an individual pixel within a set of pixels remains within plus or minus five of the average blue component value of the set of pixels, a state of consistency may be said to exist. In an embodiment, the pixels of the left and right sides of the defined bilirubin area can be examined horizontally for color values. In an embodiment, the pixels of the top of the defined bilirubin area can be examined vertically for changes in color values.

Average color values can be determined for the left, upper, and right areas of the defined bilirubin area. In an embodiment, the left, upper, and right areas of the defined bilirubin area may be combined into an overall color value. In an embodiment, both HSV and RGB color values may be determined. As a result, color values can be determined for the portion of the cropped, pixel-reduced image containing the defined bilirubin area. In an embodiment, other color models may be used to measure pixel color values. Furthermore, in an embodiment, HSV color values may alternatively be obtained by converting RGB color values.

The average color values of the portion of the image containing the defined bilirubin area can, in an embodiment, be compared with the respective color values of each of the reference color shapes. To do this, in an embodiment, color differences between the portion of the image containing the defined bilirubin area and the portions of the image containing the reference color shapes can be determined.

At high concentrations of bilirubin, the saturation component of the HSV value of portion of the image containing the defined bilirubin area can become 100% under certain light conditions or with certain cameras. Under these circumstances, in an embodiment, comparing the RGB values of the defined bilirubin area and the reference color shapes, in the image, can provide better accuracy. In an embodiment, a threshold for $HSV_{Saturation}$ (saturation threshold) can be established such that for any image for which the portion of the image containing the defined bilirubin area has an $HSV_{Saturation}$ exceeding the saturation threshold, color differences can be determined using RGB values. In an embodiment, the saturation threshold may be different for different user devices and different lighting conditions. In an embodiment, the saturation threshold may be obtained by the user device from a server based upon stored characteristics for the particular user device. In an embodiment, $HSV_{Hue}$ and $HSV_{Value}$ may also be used to determine color differences.

If the $HSV_{Saturation}$ of the portion of the image containing the defined bilirubin area does not exceed 512 the saturation threshold, the HSV color value for the portion of the image containing the defined bilirubin area can be compared 514 to the HSV color values for the portions of the image containing the reference color images. Alternatively, in an embodiment, if the saturation value of the blood sample does exceed the saturation threshold, the RGB value for the portion of the image containing the defined bilirubin area can be compared 516 to the RGB values for the portions of the image containing the reference color shapes. In an embodiment, other color models such as CMYK, HSL, Munsell, Natural Color System, Preucil, $CIELCH_{uv}$, $CIELCH_{ab}$, and CIE-CAM02 can be used to compare, in the image, the color of the defined bilirubin area and the colors of the reference color images. In an embodiment, both additive and subtractive color models can be used.

An average RGB color value may be determined by taking the square root of the sum of the squares of the red, blue, and green components of each element's RGB value. A mean RGB color value may be determined by taking the square root of the mean of the sum of the squares of the red, blue, and green components of each element's RGB value. In an embodiment, color differences between the defined bilirubin area and the reference color shapes can be determined by comparing the average RGB color value of the portion of the cropped, pixel-reduced image containing the defined bilirubin area with the RGB color values of the portions of the image containing the reference color shapes. In another embodiment, color differences in the image can be determined by comparing the mean RGB color value of the portion of the cropped, pixel-reduced image containing the defined bilirubin area with the RGB color values of the portions of the image containing the reference color shapes.

Figure 7:
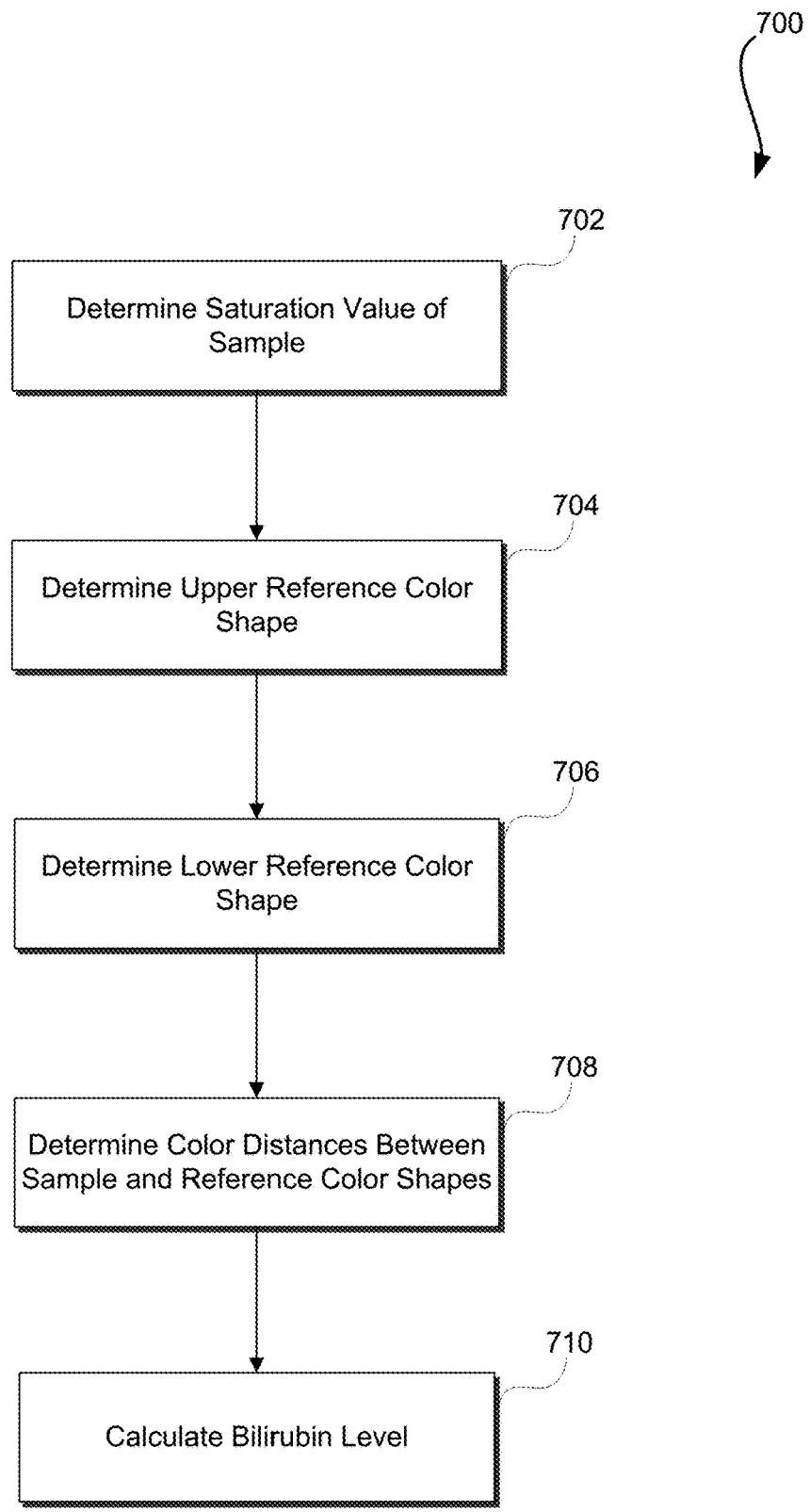
FIG. 7 shows an exemplary process for determining the bilirubin level in a blood sample in accordance with at least one embodiment.

FIG. 7 shows an illustrative example of a process 700 for determining the bilirubin level in a blood sample in accordance with at least one embodiment. In an embodiment, the $HSV_{Saturation}$ of the portion of the image containing the defined bilirubin area can be determined 702 by examining the image of a bilirubin test strip on a self-calibrating bilirubin test card. In an embodiment, the $HSV_{Saturation}$ may vary across images captured by different cameras on different user devices. As a result of determining the $HSV_{Saturation}$ of the portion of the image containing the defined bilirubin area, bracketing reference color shapes can be identified. Color differences between the defined bilirubin area of the bilirubin test strip and the bracketing reference color shapes can be determined. The bilirubin concentration of the blood sample can then be interpolated from the known bilirubin concentrations associated with the bracketing reference color shapes.

The upper reference color shape can be determined 704 by identifying the reference color shape in the image having the lowest $HSV_{Saturation}$ value greater than the average $HSV_{Saturation}$ value of the defined bilirubin area. In an embodiment, the hue component ($HSV_{Hue}$) can be constrained to be yellow. In an embodiment, the value component ($HSV_{Value}$) can be unconstrained. In an embodiment, for purposes of comparison, the hue and value components can be ignored. In an embodiment, the bilirubin test card may have any number of reference color shapes, placed anywhere on the bilirubin test card, so long as no reference color shape occludes the bilirubin test strip.

The lower reference color shape can be similarly determined 706 by identifying the reference color shape having the highest $HSV_{Saturation}$ value lower than the $HSV_{Saturation}$ value of the defined bilirubin area. In an embodiment, the hue component ($HSV_{Hue}$) can be constrained to be yellow. In an embodiment, the value component ($HSV_{Value}$) can be unconstrained. In an embodiment, for purposes of comparison, the hue and value components can be ignored.

The respective HSV color distances between the defined bilirubin area and the upper and lower reference color shapes can be determined 708. In an embodiment, let the HSV value of the defined bilirubin area be (h0, s0, v0) and the HSV value of a reference color shape be (h1, s1, v1). Let $$dh=\min(\text{abs}(h1-h0),360-\text{abs}(h1-h0))/180.0$$

$$ds=\text{abs}(s1-s0)$$

$$dv=\text{abs}(v1-v0)/255.0$$

The color distance between the defined bilirubin area and a reference color shape, in an embodiment, can be:

$$\text{distance}=\text{sqrt}(dh*dh+ds*ds+dv*dv)$$

The bilirubin value of the defined bilirubin area on the test strip can be calculated 710 by applying the color difference between the sample and the upper reference color shape against the difference between the plasma bilirubin concentration values of the two reference color shapes. Let $V_{ref1}$=the bilirubin concentration of the upper reference color shape $V_{ref2}$=the bilirubin concentration of the lower reference color shape $HSV_{ref1}$=the optically determined HSV value of the upper reference color shape $HSV_{ref2}$=the optically determined HSV value of the lower reference color shape $HSV_{Sample}$=the optically determined HSV value of the defined bilirubin area In an embodiment, the bilirubin value of the sample can then be calculated as:

$$\text{Bilirubin Concentration of the Sample}=V_{ref2}+[(V_{ref1}-V_{ref2})(HSV_{Sample}-HSV_{ref1})/(HSV_{ref1}-HSV_{ref2})]$$

Alternatively, in an embodiment, HSV color values may be obtained by converting RGB color values.

Figure 8:
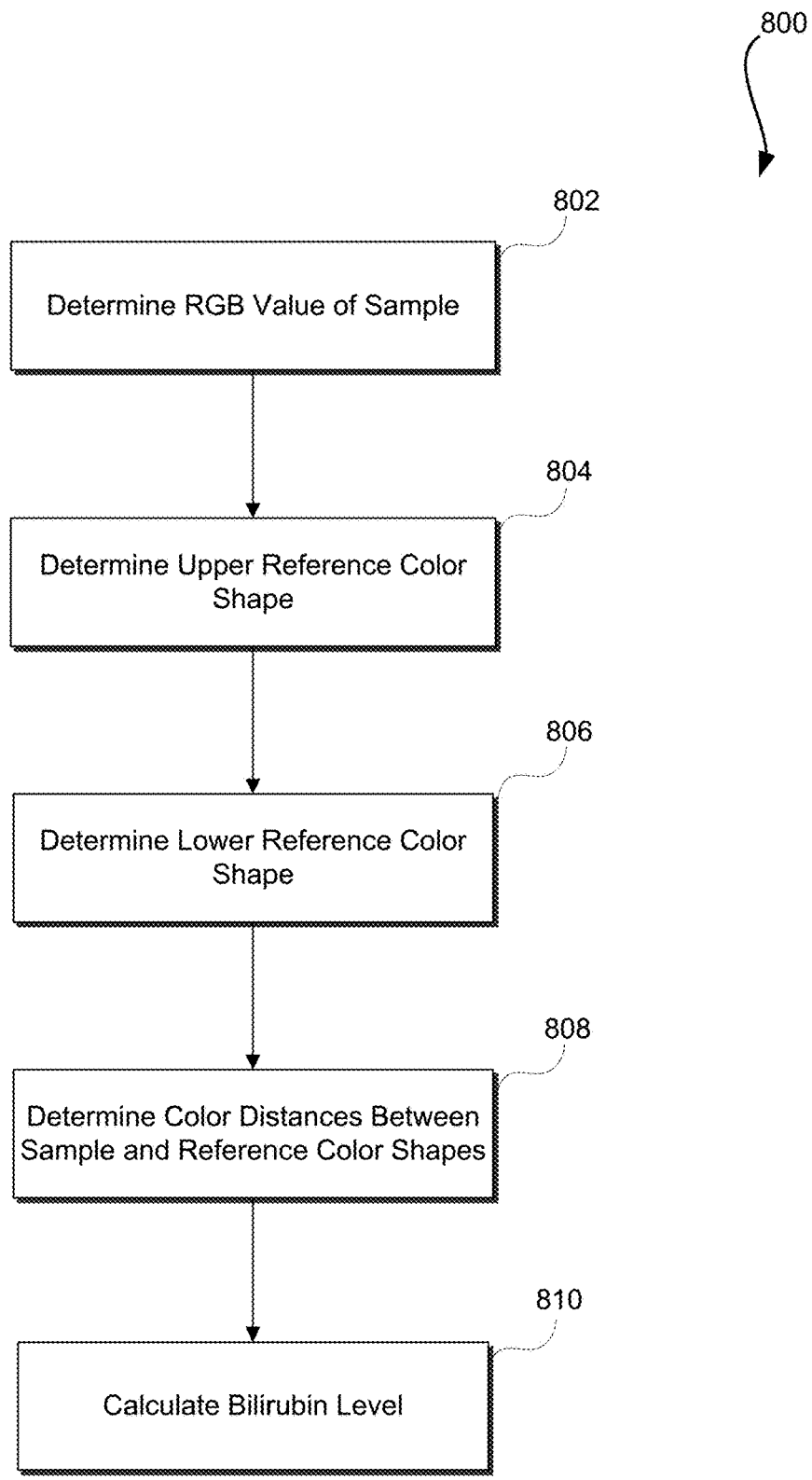
FIG. 8 shows an exemplary process for determining the bilirubin level in a blood sample in accordance with at least one embodiment.

FIG. 8 shows an illustrative example of a process 800 for determining the bilirubin level in a blood sample in accordance with at least one embodiment. In an embodiment, the RGB color value of a blood sample can be determined 802 by examining the image of a bilirubin test strip on a self-calibrating bilirubin test card. In an embodiment, the RGB color value may vary across images captured by different cameras on different user devices. As a result of determining the RGB color value of the defined bilirubin area, bracketing reference color shapes can be identified. Color differences between the defined bilirubin area of the bilirubin test strip and the bracketing reference color shapes can be determined. The bilirubin concentration of the blood sample can then be interpolated from the known bilirubin concentrations associated with the bracketing reference color shapes.

The upper reference color shape can be determined 804 by identifying the reference color shape having the lowest RGB value greater than the RGB value of the defined bilirubin area. In an embodiment, the bilirubin test card may have any number of reference color shapes, placed anywhere on the bilirubin test card, so long as no reference color shape occludes the bilirubin test strip.

The lower reference color shape can be determined 806 by identifying the reference color shape having the highest RGB value lower than the RGB value of the defined bilirubin area. In an embodiment, the blue component ($RGB_{blue}$) can be ignored. The respective color distances between the blood sample and the upper and lower reference color shape can then be determined 808. The bilirubin value of the blood sample can then be calculated 810 by applying the color difference between the defined bilirubin area and the upper reference color shape against the difference between the plasma bilirubin concentration values of the two reference color shapes. Let $V_{ref1}$=the bilirubin concentration of the upper reference color shape $V_{ref2}$=the bilirubin concentration of the lower reference color shape $RGB_{ref1}$=the optically determined RGB value of the upper reference color shape $RGB_{ref2}$=the optically determined RGB value of the lower reference color shape $RGB_{Sample}$=the optically determined RGB value of the defined bilirubin area In an embodiment, the bilirubin value of the sample can then be calculated as:

$$\text{Bilirubin concentration of the sample}=V_{ref2}+[(V_{ref1}-V_{ref2})(RGB_{Sample}-RGB_{ref1})/(RGB_{ref1}-RGB_{ref2})]$$

FIG. 9 shows illustrative examples of other embodiments of self-calibrating bilirubin test cards. A simple and low cost test can involve evaluating the color of the sclera area of the eye. Yellowing of the normally white area of the eye can indicate a high amount of bilirubin. In a similar approach as with a blood sample, an image of the eye may be processed along with reference color shapes. As with the blood sample, in an embodiment, self-calibrating an image of the eye may allow calculation of the amount of yellowing in the eye using reference color shapes corresponding to known values of bilirubin. A self-calibrating bilirubin test card 902 for the eye can include a cut-out 904 and a set of reference color shapes 908-910. The cut-out 904 may be circular. Alternatively, the cut-out may be in any shape that allows an image of the eye to be obtained. Placing the test card 902 such that the infant's eye can be viewed through the cut-out 904 allows a single photographic image to contain both the eye and the reference color shapes 908-910.

In an embodiment, the bilirubin test card 902 can be made of semi-gloss paper, although a bilirubin test card can be constructed from any type of paper, plastic, metal, or other substance. In an embodiment, the bilirubin test card can be reusable, with detachable or replaceable reference color shapes. The bilirubin test card may also employ a detachable test strip, with a new test strip attached for each test. In an embodiment, a bilirubin test card may have any dimensions that allow its image to be captured by the camera of a user device. For example, a bilirubin test card may be rectangular or circular.

In an embodiment, the reference color shapes 908-910 can have increasingly darker values of yellow, with reference color shape 908 having the lightest shade and saturation and reference color shape 910 having the darkest shade and saturation. In an embodiment, the yellowness and saturation can increase from reference color shapes 908-910 in a clockwise direction beginning with reference color shape 908 and ending with reference color shape 910. Alternatively, in an embodiment, the yellowness and saturation can increase from reference color shapes 910 to 908 in a counter-clockwise direction beginning with reference color shape 910 and ending with reference color shape 908. In an embodiment, the reference color shapes 910 to 908 may be placed anywhere on the bilirubin test card and their location and coordinates communicated to the user device. In an embodiment, some of the reference color shapes 908-918 may be white.

Transcutaneous bilirubin (TcB) can be the measurement of bilirubin at the skin. TcB can be calculated for fairskinned infants. As a naturally occurring phenomena, bilirubin concentrations may decrease from the top of the head to the toes. Thus, readings of TcB at the skin of the head may show a higher level of bilirubin than at the leg. Calculation of the difference between readings taken at the head, chest, and leg may allow a calculation of bilirubin levels, and thus comparing the skin tone of an infant, at multiple locations on its body, with known reference color values can be used to determine the different levels of bilirubin. Furthermore, blanching the skin by depressing it, allows the bilirubin coloration to show.

The self-calibrating TcB test card 912, in an embodiment, can possess two holes 914 and 916 cut in the card. The self-calibrating TcB test card 912 may allow simultaneous correction and capture of an image of a skin region thorough the first hole 914 of the card. In an embodiment, the second hole 916 of the card may be covered with a plastic barrier. The plastic barrier may push against the skin, causing the skin to blanch and present the color of the blanched skin. Comparison of the blanched and non-blanched skin regions can be made against the reference color shapes 908-910. In an embodiment, comparison of the blanched skin region with the reference color shapes 908-910 can provide an indication of bilirubin level. Blanched and unblanched flesh can present differences in skin tone. These differences in skin tone can be calculated into the determination of bilirubin level. In an embodiment, the blanched skin visible through the second hole 916 can be analogous to the bilirubin test strip 204 of FIG. 2. In an embodiment, any number of holes may be made in the test card.

In an embodiment, the self-calibrating TcB test card 912 can be made of semi-gloss paper, although a TcB test card can be constructed from any type of paper, plastic, metal, or other substance. In an embodiment, the TcB test card can be reusable, with detachable or replaceable reference color shapes. The TcB test card may also employ a detachable test strip, with a new test strip attached for each test. In an embodiment, a TcB test card may have any dimensions that allow its image to be captured by the camera of a user device. For example, a test card may be rectangular or circular.

In an embodiment, the reference color shapes 918-920 can have increasingly darker values of yellow, with reference color shape 918 having the lightest shade and saturation and reference color shape 920 having the darkest shade and saturation. In an embodiment, the yellowness and saturation can increase from reference color shapes 918-920 in a clockwise direction beginning with reference color shape 908 and ending with reference color shape 918. Alternatively, in an embodiment, the yellowness and saturation can increase from reference color shapes 920 to 918 in a counter-clockwise direction beginning with reference color shape 920 and ending with reference color shape 918. In an embodiment, some of the reference color shapes 918-920 may be white. In an embodiment, a different number of white reference color shapes at the top and bottom of the TcB test card can indicate the proper orientation of the TcB test card.

In infants, a complication that may occur when calculating bilirubin levels from TcB can be caused by the natural pigmentation of the skin. The amount of pigmentation can be factored in the overall calculation of the bilirubin levels. However, the tongue lacks pigmentation. Taking a photo image of the tongue may allow calculation of the bilirubin levels without the need to compensate for individual infant pigmentation levels. A difficulty in obtaining a sample of the tongue may result from not having a template small enough to blanch the tongue for the comparison, as well as capturing the correction images.

The self-calibrating TcB test card 922, in an embodiment, can possess a hole 924 cut in the center of the card. In an embodiment, the hole 924 may be placed elsewhere on the card. The self-calibrating TcB test card 922 may allow simultaneous correction and capture of a tongue region thorough the hole 924 of the card. In an embodiment, the hole 924 may be divided into two sections. The left half 926 of the hole 924 may be open and allow the tongue flesh to protrude. The right half 928 may be closed with clear plastic, which, pushing against the tongue, may blanch the tongue and present the color of the blanched tongue. The blanched and non-blanched tongue regions can be compared with the reference color shapes 930. In an embodiment, comparison of the blanched skin region with the reference color shapes 930 can provide an indication of bilirubin level. In an embodiment, the blanched skin visible through the right half 928 of the hole 916 can be analogous to the bilirubin test strip 204 of FIG. 2.

In an embodiment, the reference color shapes 930-932 can have increasingly darker values of yellow, with reference color shape 930 having the lightest shade and saturation and reference color shape 932 having the darkest shade and saturation. In an embodiment, the yellowness and saturation can increase from reference color shapes 930 to 932 in a clockwise direction beginning with reference color shape 930 and ending with reference color shape 932. Alternatively, in an embodiment, the yellowness and saturation can increase from reference color shapes 932 to 930 in a counter-clockwise direction beginning with reference color shape 932 and ending with reference color shape 930. In an embodiment, some of the reference color shapes 930-932 may be white. In an embodiment, a different number of white reference color shapes at the top and bottom of the self-calibrating TcB test card 922 can indicate the proper orientation of the self-calibrating TcB test card 922.

In an embodiment, the self-calibrating TcB test card 922 can be made of semi-gloss paper, although a test card can be constructed from any type of paper, plastic, metal, or other substance. In an embodiment, the self-calibrating TcB test card 922 can be reusable, with detachable or replaceable reference color shapes. The self-calibrating TcB test card 922 may also employ a detachable test strip, with a new test strip attached for each test. In an embodiment, a self-calibrating TcB test card 922 may have any dimensions that allow its image to be captured by the camera of a user device. For example, a self-calibrating TcB test card 922 may be rectangular or circular.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives. Additionally, elements of a given embodiment should not be construed to be applicable to only that example embodiment and therefore elements of one example embodiment can be applicable to other embodiments. Additionally, in some embodiments, elements that are specifically shown in some embodiments can be explicitly absent from further embodiments. Accordingly, the recitation of an element being present in one example should be construed to support some embodiments where such an element is explicitly absent.

What is claimed is:

1. A plasma bilirubin assay system, comprising:
a test card, the test card including:
a grid overlay, the grid overlay including:
a bilirubin test strip upon which a blood sample has been deposited, the bilirubin test strip centered on the test card, the bilirubin test strip comprising a plasma separator and a lateral flow membrane, the plasma separator filtering red blood cells from the blood sample and resulting in plasma on the lateral flow membrane; and
a set of calibration images surrounding the bilirubin test strip, the set of calibration images having known saturation and red/green/blue (RGB) values, the known saturation and RGB values corresponding to specific concentrations of bilirubin in plasma; and
a mobile device, the mobile device comprising a camera;
the mobile device configured to:
capture an image of the test card with the camera;
generate a cropped image of the test card that includes at least the set of calibration images and the plasma on the lateral flow membrane;
reduce pixel density of the cropped image;
identify borders of the set of calibration images;
identify borders of the plasma on the lateral flow membrane;
determine an area of the plasma on the lateral flow membrane by:
from a top border of the plasma on the lateral flow membrane, scanning down vertically, determining a uniform value of consecutive vertical pixels;
from a left border of the plasma on the lateral flow membrane, scanning right, determining a uniform value of consecutive horizontal pixels; and
from a right border of the plasma on the lateral flow membrane, scanning left, determining a uniform value of consecutive horizontal pixels;
determine a saturation value of each calibration image of the set of calibration images;
determine a saturation value of the plasma on the lateral flow membrane;
determine an upper calibration image, the upper calibration image being a calibration image having a lowest saturation value higher than the saturation value of the plasma on the lateral flow membrane;
determine a lower calibration image, the lower calibration image being a calibration image having a highest saturation value lower than the saturation value of the plasma on the lateral flow membrane;
determine a first color distance between the saturation value of the upper calibration image and the saturation value of the plasma on the lateral flow membrane;
determine a second color distance between the saturation value of the lower calibration image and the saturation value of the plasma on the lateral flow membrane;
determine an average of the first color distance and the second color distance;
determine a bilirubin level of the plasma on the lateral flow membrane based at least in part on the average of the first color distance and the average of the second color distance; and
report the bilirubin level of the plasma on the lateral flow membrane.

2. The plasma bilirubin assay system of claim 1, wherein as a result of a determination that the saturation value of the plasma exceeds a saturation threshold:
determine an average RGB value of each calibration image of the set of calibration images;
determine an average RGB value of the plasma on the lateral flow membrane;
determine a second upper calibration image, the second upper calibration image being a calibration image having a lowest average RGB value higher than the average RGB value of the plasma on the lateral flow membrane;
determine a second lower calibration image, the second lower calibration image being a calibration image having a highest average RGB value lower than the average RGB value of the plasma on the lateral flow membrane;
determine a third color distance between the average RGB value of the second upper calibration image and the average RGB value of the plasma on the lateral flow membrane; and
determine a fourth color distance between the average RGB value of the second lower calibration image and the average RGB value of the plasma on the lateral flow membrane;
determine an average of the third color distance and the fourth color distance;
determine a second bilirubin level of the plasma on the lateral flow membrane based at least in part on the average of the third color distance and the average of the fourth color distance; and
report the second bilirubin level of the plasma on the lateral flow membrane.

3. The plasma bilirubin assay system of claim 1, wherein the bilirubin test strip is detachable from the test card.

4. The plasma bilirubin assay system of claim 1, wherein the image of the test card is cropped using computer vision techniques on the mobile device.

5. The plasma bilirubin assay system of claim 1, wherein a color model other than saturation is used to determine the first color distance and the second color distance, the color model including RGB, CMYK, HSL, Munsell, Natural Color System, Preucil, CIELCHuv, CIELCHab, and CIECAM02.

6. The plasma bilirubin assay system of claim 1, wherein white calibration images indicate an orientation of the test card.

7. A plasma bilirubin assay system, comprising:
a test card, the test card including:
a grid overlay, the grid overlay including:
a bilirubin test strip upon which a blood sample has been deposited, the bilirubin test strip centered on the test card, the bilirubin test strip comprising a plasma separator and a lateral flow membrane, the plasma separator filtering red blood cells from the blood sample and resulting in plasma on the lateral flow membrane; and
a set of one or more calibration images; and
a mobile device, the mobile device comprising a camera;
the mobile device configured to:
capture an image of the test card with the camera, the image including at least the set of one or more calibration images and the plasma on the lateral flow membrane;
determine a saturation value of each calibration image of the set of one or more calibration images;
determine a saturation value of the plasma on the lateral flow membrane;

determine an upper calibration image, the upper calibration image being a calibration image having a lowest saturation value higher than the saturation value of the plasma; and determine a lower calibration image, the lower calibration image being a calibration image having a highest saturation value lower than the saturation value of the plasma on the lateral flow membrane;

determine a first color distance between the saturation value of the upper calibration image and the saturation value of the plasma on the lateral flow membrane;

determine a second color distance between the saturation value of the lower calibration image and the saturation value of the plasma on the lateral flow membrane; and determine a bilirubin level of the plasma on the lateral flow membrane based at least in part on an average of the first color distance and the average of the second color distance.

8. The plasma bilirubin assay system of claim 7, wherein the set of one or more calibration images have known saturation and red/green/blue (RGB) values, the known saturation and RGB values corresponding to specific concentrations of bilirubin in plasma.

9. The plasma bilirubin assay system of claim 7, wherein the saturation value of the plasma on the lateral flow membrane is determined, at least in part by:

from a top border of the plasma on the lateral flow membrane, scanning down vertically, determining a uniform value of consecutive vertical pixels;

from a left border of the plasma on the lateral flow membrane, scanning right, determining a uniform value of consecutive horizontal pixels; and from a right border of the plasma on the lateral flow membrane, scanning left, determining a uniform value of consecutive horizontal pixels.

10. The plasma bilirubin assay system of claim 7, wherein the set of one or more calibration images surrounds the bilirubin test strip.

11. The plasma bilirubin assay system of claim 7, wherein the set of one or more calibration images are varying shades of yellow.

12. The plasma bilirubin assay system of claim 7, wherein the set of one or more calibration images consists essentially of a single calibration image.

13. The plasma bilirubin assay system of claim 7, wherein the image of the test card is cropped to exclude a portion of the bilirubin test strip containing the red blood cells.

14. The plasma bilirubin assay system of claim 7, wherein the image of the test card is cropped to include only the calibration images and the plasma on the lateral flow membrane.

15. A plasma bilirubin assay system, comprising:
a test card, the test card including:
a overlay, the overlay including:
a bilirubin test strip upon which a blood sample has been deposited, the bilirubin test strip centered on the test card, the bilirubin test strip comprising a plasma separator and a lateral flow membrane, the plasma separator filtering red blood cells from the blood sample and resulting in plasma on the lateral flow membrane; and
a set of calibration images; and
a device, the device comprising a camera, the device configured to:
capture an image of the test card with the camera;
determine a set of saturation values corresponding to the set of calibration images;
determine a saturation value of the plasma on the lateral flow membrane;
determine an upper calibration image and a lower calibration image, the upper calibration image and lower calibration image being two calibration images having saturation values closest to the saturation value of the plasma on the lateral flow membrane, the upper calibration image having a greater saturation than the lower calibration image; and
determine a bilirubin level of the plasma on the lateral flow membrane based at least in part on interpolating:
a saturation color distance between the upper calibration image and the plasma on the lateral flow membrane; and
a saturation color distance between the lower calibration image and the plasma on the lateral flow membrane.

16. The plasma bilirubin assay system of claim 15, wherein the lateral flow membrane comprises a nitrocellulose membrane.

17. The plasma bilirubin assay system of claim 15, wherein the plasma separator is comprised of polyvinylidene difluoride.

18. The plasma bilirubin assay system of claim 15, wherein the plasma separator is comprised of glass fiber.

19. The plasma bilirubin assay system of claim 15, wherein the set of calibration images is arranged in rows.

20. The plasma bilirubin assay system of claim 15, wherein the set of calibration images surrounds the bilirubin test strip.

* * * * *